United States Patent [19]

Heilmann et al.

[11] Patent Number: 5,713,850
[45] Date of Patent: Feb. 3, 1998

[54] APPARATUS FOR CONTROLLING A FLUID FLOW

[75] Inventors: Klaus Heilmann, St. Wendel; Josef Herrmann, Eppelborn; Claus Jessen, Otzenhausen; Helmut Schmidt, Oberthal; Christian Schwegmann; Michael Zimmermann, both of St. Wendel, all of Germany

[73] Assignee: Fresenius AG, Bad Homburg, Germany

[21] Appl. No.: 567,561

[22] Filed: Dec. 5, 1995

[30] Foreign Application Priority Data

Dec. 9, 1994 [DE] Germany .................. 44 43 714.5

[51] Int. Cl.[6] .................................................. A61M 1/00
[52] U.S. Cl. .................. 604/28; 604/29; 604/32; 137/625.46
[58] Field of Search .............. 137/625.46, 625.11; 604/246, 248, 249, 29, 32, 33, 28; 251/251

[56] References Cited

U.S. PATENT DOCUMENTS

| | | |
|---|---|---|
| 3,468,344 | 9/1969 | Sanford . |
| 4,073,471 | 2/1978 | Lehtinen . |
| 4,137,945 | 2/1979 | Cutts . |
| 4,470,429 | 9/1984 | Johnson . |
| 4,601,307 | 7/1986 | Johnson . |
| 4,865,078 | 9/1989 | Ensign . |
| 4,892,984 | 1/1990 | Clark et al. . |
| 4,934,408 | 6/1990 | Christopherson . |
| 4,950,230 | 8/1990 | Kendell . |

Primary Examiner—Mark Bockelman
Attorney, Agent, or Firm—Henry M. Feiereisen

[57] ABSTRACT

Apparatus for controlling a fluid flow includes a housing having a first fitting for connection of a tube and at least one further fitting for detachable securement of a coupling piece of a peritoneal catheter. Accommodated in the housing is a rotary valve which is indexable in predetermined positions to selectively establish a fluid communication between the fittings. Associated with one of the fittings is at least one closure member which is acted upon by the rotary valve for displacement in a radial direction to open and close a passage to the peritoneal catheter.

13 Claims, 5 Drawing Sheets

APPARATUS FOR CONTROLLING A FLUID FLOW

BACKGROUND OF THE INVENTION

The present invention refers to an apparatus for controlling a fluid flow, and in particular to an apparatus of a type having a housing formed with at least one fitting for permanent securement of a tube and at least one further fitting for detachable connection of another tubular element such as a coupling piece or connecting piece of a peritoneal catheter, and a rotary valve unit, called connector, rotatable in the housing for controlling a fluid passageway therethrough.

Devices for connecting several tubes are widely used. For a three tubes arrangement, the linking is generally effected by a Y-pipe. Through suitable turning of the Y-pipe, two tubes can be connected at one time. Such devices are also used for attachment to the peritoneal catheter of a patient during peritoneal dialysis.

Peritoneal dialysis is a type of dialysis therapy that utilizes the membrane in a patient's peritoneal cavity for the purpose of separating waste products from the patient's fluid system. One type of peritoneal dialysis is referred to as continuous ambulatory peritoneal dialysis (CAPD) in which a dialysis solution is introduced from a solution bag into the patient's peritoneal cavity by a peritoneal catheter, with the dialysis solution exhibiting a concentration gradient in relation to body-own fluids. Toxic substances enter the peritoneal cavity via the peritoneum that acts as the membrane. After a few hours, spent fluid is drained from the peritoneal cavity to a drain bag, and fresh fluid is infused from another solution bag. To regulate the fluid flow through the tubing set, a coupler is secured to the abdomen-side section of the catheter and connected to a Y-pipe which communicates with a bag containing fresh dialysis solution and with a bag receiving spent dialysis solution.

A problem of the continuous ambulatory peritoneal dialysis is the risk of introducing germs into the peritoneal cavity via the catheter that is guided through the abdominal wall. This may cause peritonitis. Various connection elements have been proposed to enable a rapid coupling of the Y-pipe to the peritoneal catheter and to reduce a contamination of the fluid-carrying ports of the connection system and of the abdominal-side catheter section.

European publication EP-OS 0 098 103 discloses a catheter coupling for ambulatory peritoneal dialysis, which includes a female coupling piece of special steel or titanium that remains on the abdomen-side catheter section of the patient, and a male coupling piece that is made of a thermoplast suitable for medical purposes and forms a disposable item which is replaced after each change of dialysis solution. The two coupling pieces bear upon each other on surfaces in form of Luer cones. This coupling mechanism has the drawback that the female coupler after exchange of the dialysis solution and removal of the Y-pipe must be sealed together with the male coupling piece by a separate closure member in order to seal the patient-side catheter section and to avoid a contamination. The required insertion of the closure member, normally a plug, and manipulation of the female coupler represents, however, an additional source of contamination which should be avoided.

European publication EP-OS 0 073 432 describes a similar connecting mechanism in which a tubular piercing pin penetrates a pierceable diaphragm disposed in a coupling piece to effect the connection with the catheter. The point of connection is additionally enveloped by a ring-shaped sponge that is soaked with disinfectant to avoid infection. Such a connection mechanism is relatively complicated and the sponge is difficult to handle. Moreover, the sponge is expensive to produce and has only a limited storage capability. Also, there is a possibility that excessive amounts of disinfectant migrate into the peritoneal cavity of the patient.

U.S. Pat. No. 5,057,074 describes a medical container replacing method in which the connection between the catheter and the container for fresh dialysis solution is cut so that the catheter piece together with the complete connector assembly, i.e. tubular coupler, remains attached to the abdomen-side catheter portion of the patient. At replacement of dialysis solution, the retained catheter portion is removed and a new connection is formed. Thus, the patient is required to carry the catheter section between two exchanges of dialysis solution. This, however, is a nuisance and uncomfortable for the patient. Moreover, the catheter section that remains attached to the body of the patient is relatively long so that it may get caught in the patient's clothing and become loose, thereby causing a great risk of contamination as well as a dangerous and unhygienic discharge of dialysis solution from the peritoneal cavity.

U.S. Pat. No. 4,821,996 describes a connector which includes a housing with two fittings for fixed connection of tubes, and with a third fitting for securement to the peritoneal catheter. The connector is cylindrical in shape and includes a rotary valve system which has a flow controlling selection ring that can be rotated in only one direction for closing and opening fluid flow conduits in a predetermined sequence to carry out a drain and fill cycle as required by the patient. Even though a fluid flow control valve of this type is able to reduce the frequency of mishaps during peritoneal dialysis, the necessity to close the abdominal-side catheter portion by hand after exchange of dialysis solution harbors an increased risk of infection.

SUMMARY OF THE INVENTION

It is an object of the present invention to provide an improved apparatus for controlling a fluid flow, obviating the afore-stated drawbacks.

In particular, it is an object of the present invention to provide an improved fluid flow control valve unit which substantially eliminates a risk of contamination during closure of a port.

These objects, and others which will become apparent hereinafter, are attained in accordance with the present invention by incorporating within the housing at least one displaceable closure member and by providing a rotary valve unit including a rotatable assembly which upon rotation effects a radial movement of the closure member.

A valve unit according to the present invention, also called "connector", is suitable for attachment to the peritoneal catheter of the patient either directly or via a coupling piece and utilizes the rotation of the rotatable assembly to effect a radial displacement of the closure member relative to the coupling piece to seal the catheter, thereby eliminating a manual handling and minimizing a risk of contamination.

The drain and fill cycle during peritoneal dialysis is carried out in a series of predetermined successive steps. In an initial step, spent but sterile fluid is drained to flush away germs which may be present in the connector. Subsequently, in a second step, solution is washed from the storage bag via the connector to the outlet to irrigate the entire system with fresh and sterile solution, while the third tube branch to the peritoneal cavity is sealed off. In a third step, fresh discharge opening is filled into the peritoneal cavity, with the drain being sealed off. A continuous turning of the catheter coupling closes the access to the abdomen by an integrated closure member, without requiring the patient to touch the closure member. After closing the coupler, the connector is unscrewed and discarded together with the storage bag and the drain bag. The coupling piece (or connecting piece) which still remains attached to the catheter and thus to the patient is normally secured additionally by a protective cap. Only upon renewed peritoneal dialysis is the patient-side tube clamped, the complete coupling piece removed and a new connector including coupling piece reattached. The clamp is released only during the second step as described above.

With the valve unit according to the present invention, the risk of contamination is substantially eliminated because the rotation of the rotatable assembly is exploited to attach the closure member onto the coupling piece of the peritoneal catheter.

Preferably, the housing is generally cylindrical in shape, with the rotatable assembly including a grip portion which is connected to a rotatable blocking element of generally cylindrical configuration which normally prevents a fluid flow between two fittings and is formed with lateral openings to allow a fluid connection between two fittings upon suitable rotation of the grip portion.

The valve unit may include several closure members— one closure member for each fitting—which are movable in radial direction by the rotation of the rotatable assembly for opening and closing a passage through the fittings. By suitably controlling the position of the blocking element and of the closure members, the flow rate of fluid through the passageway can be controlled.

When forming the housing with three fittings, e.g. for connection to the peritoneal catheter, on the one hand, and to the solution bag and drain bag, on the other hand, the operation of the rotatable assembly is such that maximal two of the three fittings are connected with each other at one time.

Preferably, the conversion of the rotation of the rotatable assembly into a radial displacement of the closure member is effected by a cam which acts on the closure member. Suitably, the closure member may be in form-fitting connection with the cam.

According to another feature of the present invention, the valve unit is equipped with an extractor by which the closure member can be automatically withdrawn from the catheter without requiring a manual manipulation by the patient. Preferably, the extractor is formed by a track connected to the valve unit, with the plug being secured on the track so as to move in radial direction upon rotation of the rotatable assembly. The provision of an extractor eliminates a need to clamp the tube and to remove the closure member by hand, before attaching a new connector. After reattaching a connector, the closure member is automatically withdrawn from the catheter by the rotation of the rotatable assembly shortly before draining fluid from the peritoneal cavity into the drain bag.

In accordance with another feature of the present invention, the connector is secured at the beginning of the peritoneal dialysis to the coupling piece by a protective cap. Since, at this stage, the connector is already attached also to a bag filled with fresh dialysis solution and to an empty bag for receiving spent fluid, a danger of a mix-up is prevented and the process steps are predetermined. Advantageously, the protective cap is placed over the closure member.

As the individual process steps must be followed in a predetermined sequence which cannot be altered, the rotary valve is rotatable in only one direction of rotation, whereby each process step is monitored optically, e.g. by means of a flow indicator in the grip portion, and/or in a tactile fashion, e.g. by means of an inner cam with latching elements.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
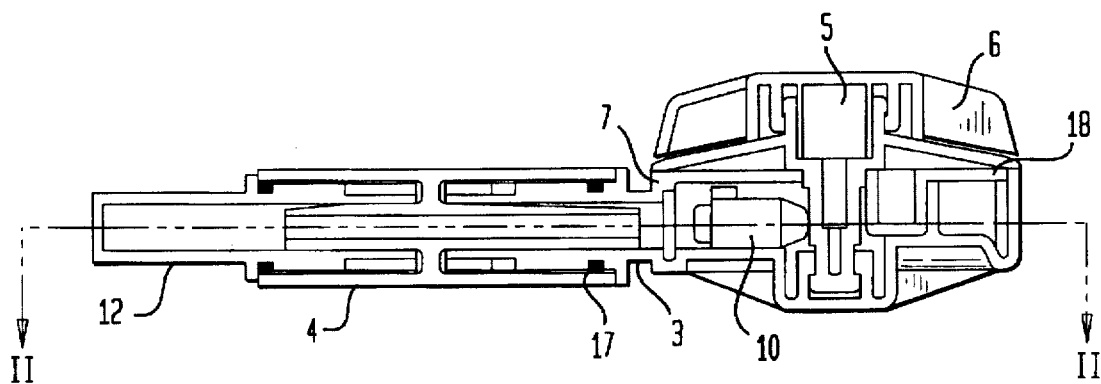
FIG. 1 is a vertical section of one embodiment of an apparatus for controlling a fluid flow in accordance with the present invention.

Throughout all the Figures, the same or corresponding elements are generally indicated by the same reference numerals.

Figure 2:
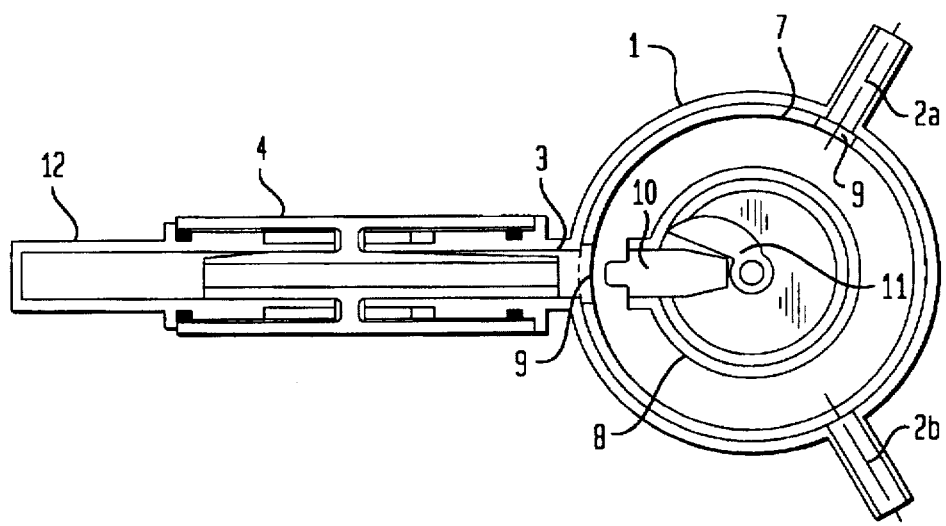
FIG. 2 is a horizontal section of the apparatus of FIG. 1, taken along the line II—II.

Turning now to the drawing, and in particular to FIGS. 1 and 2, there is shown a valve apparatus in accordance with the present invention for controlling a fluid flow including a housing 1 which is generally cylindrical in shape and is formed with two fittings 2a, 2b spaced from each about the circumference and allowing secure connection of respective tubes. When using the valve apparatus for peritoneal dialysis, a container filled with fresh dialysis solution would be secured to the fitting 2b while an empty bag for receiving spent fluid is secured to the fitting 2a.

The housing 1 is further provided with a third fitting 3 for securement of a coupling part 4 of e.g. a peritoneal catheter 12 of a patient. The connection between the fitting 3 and the coupling part 4 can be effected by a suitable snap-in mechanism which is sealed by O-rings 17.

Securely placed in the housing 1 is a rotary valve, generally designated by reference numeral 5 for controlling a fluid flow. The valve 5 includes a rotatable assembly in form of a grip portion 6 and a blocking element 7 which is generally cylindrical in shape and is able to seal a fluid flow between the fittings 2, 2b, 3. The blocking element 7 is connected, e.g. in form-fitting manner, to the grip portion 6 and secured within the housing 1 by an axial support 8 of hollow cylindrical configuration which is formed integrally with the housing 1. A cover plate 18 of the blocking element 7 seals the blocking element from the grip portion 6 and resiliently bears upon the support 8. Suitably the outside of the grip portion 6 displays a symbolic illustration of the fluid flow for informative purposes.

As shown in particular in FIG. 2, the blocking element 7 is formed with two openings 9 which are spaced about its circumference to allow a fluid flow between two of the three fittings 2a, 2b, 3 of housing 1 when aligning the openings 9 with the respective fittings through selective positioning of the blocking element 7. In the exemplified illustration of FIG. 2, the blocking element 7 is positioned in such a manner that a fluid flow between the fittings 3 and 2a is effected to allow a flow of spent fluid from the peritoneal cavity to the drain bag communicating with the fitting 2a.

As further shown in FIGS. 1 and 2, the housing 1 accommodates a closure member in form of a plug 10 which is secured by the support 8 (FIG. 2) and is radially displaceable in direction of the coupling part 4 to open or close a fluid flow to the peritoneal catheter. The radial displacement of the plug 10 is effected by a cam 11 which is held within the hollow cylindrical support 8 and secured to the blocking element 7. Thus a rotation of the grip portion 6 turns the blocking element 7 and thus the cam 11 which imparts a motion to the plug 10 in a radial direction.

Persons skilled in the art will understand that the rotary valve 5 should further include a stop member to prevent an unintentional removal of the plug 10 through further rotation of the blocking element 7 once the plug 10 is pushed in place, as each process step should be precisely assignable to a position of the rotary valve 5. In addition, the rotary valve 5 should also be provided with a safety mechanism for preventing an unintentional detachment of the valve from the coupling piece and/or for preventing an unintentional detachment of the coupling piece from a peritoneal catheter. An example of such a safety mechanism is a screw cap. Also, the blocking element 7 must be formed with a passageway for allowing displacement of the plug 10 in radial direction to close the fitting 3 when the blocking element 7 is so positioned as to connect the fittings 2a and 2b. These features are however not shown in the foregoing drawings for sake of simplicity.

FIGS. 3 to 9 illustrate schematically by way of partly sectional views various steps for carrying out a bag exchange of the peritoneal dialysis.

Figure 3:
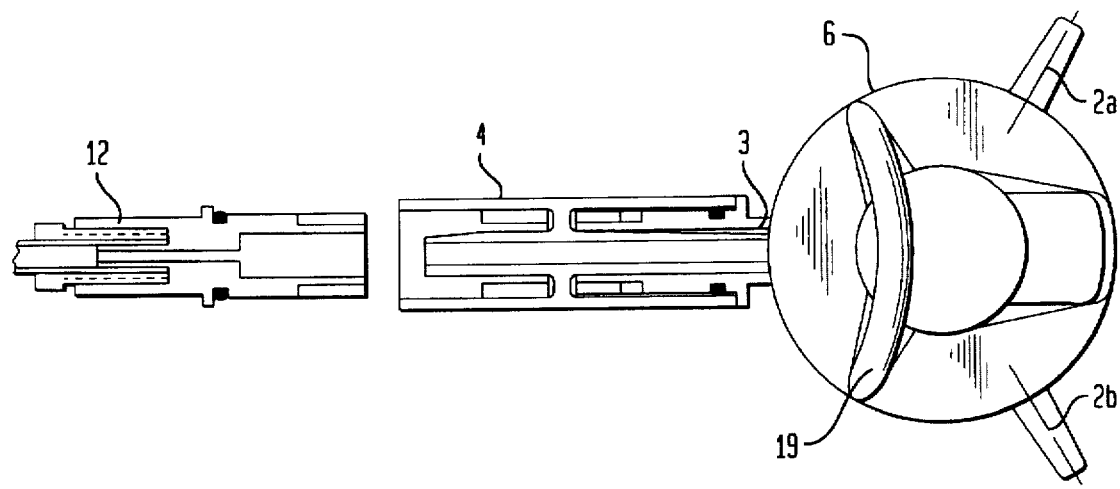
FIGS. 3 to 9 illustrate schematically by way of partly sectional views various steps for carrying out a bag exchange of the peritoneal dialysis.

In FIG. 3, the blocking element 7 of the rotary valve 5 occupies a first index position in which all fittings 2a, 2b, 3 are blocked. At this stage, the coupling part 4 of the rotary valve 5 that is secured to the fitting 3 is connected to the peritoneal catheter 12. A not shown empty drain bag is connected to fitting 2a and a not shown bag containing fresh dialysis solution is connected to fitting 2b.

Figure 4:
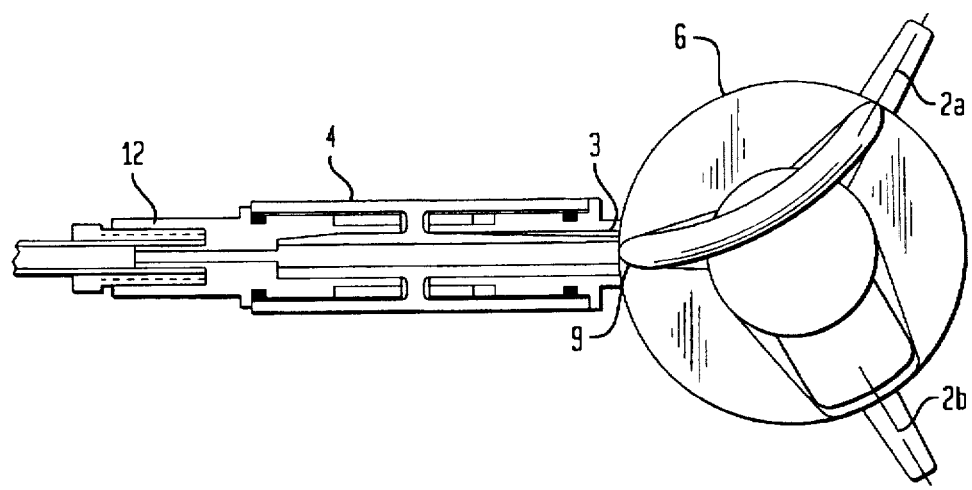

FIG. 4 shows the blocking element 7 in a second index position in which the blocking element 7 is turned to align the openings 9 with the fittings 2a, 3 to place the catheter 12 in fluid communication with the empty bag through passageway 19 of the rotary valve 5, permitting spent dialysis fluid to be drained from the peritoneal cavity to the empty bag for collection.

Figure 5:
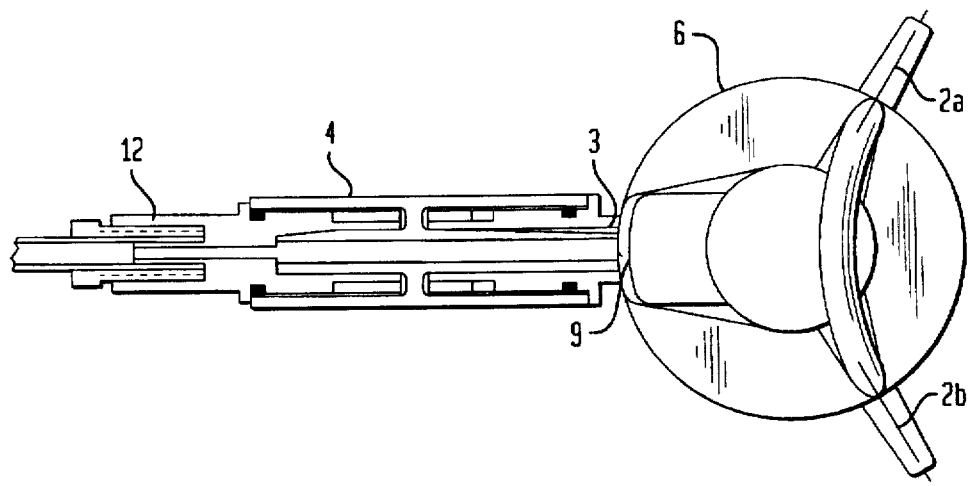

FIG. 5 shows a third index position of the blocking element 7 to place the fittings 2a, 2b in fluid communication so that the fluid passageways of the rotary valve can be flushed with fresh dialysis solution flowing from the solution bag to the drain bag. The access to the peritoneal catheter 12 is shut.

Figure 6:
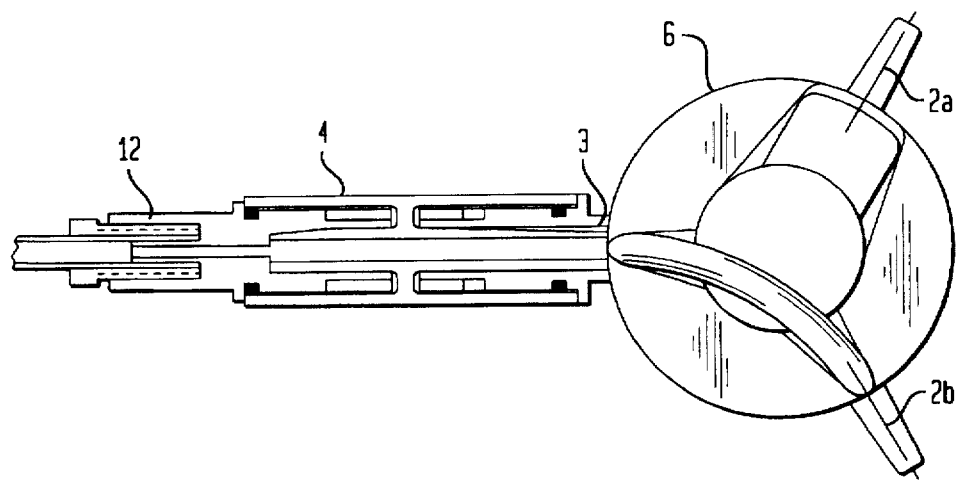

FIG. 6 shows a fourth index position of the blocking element 7 to place the fittings 2a 3 in fluid communication so that fresh dialysis solution can flow from the solution bag through passageway 19 and peritoneal catheter 12 into the peritoneal cavity of the patient. In general, the fill portion of the cycle is effected under the influence of gravity.

Figure 7:
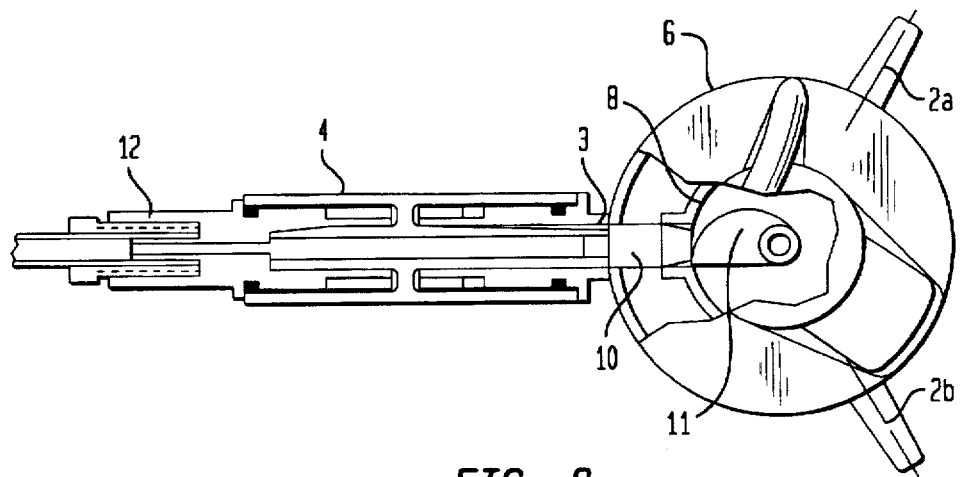
Figure 8:
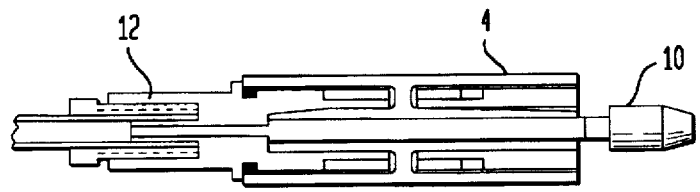

FIG. 7 shows a fifth index position of the blocking element 7 in which fluid flow through all fittings 2a, 2b, 3 is blocked. At the same time, the rotation of the blocking element 7 is followed by the cam 11 which now impacts the plug 10 along its tapered or slanted surface to force a displacement of the plug 10 in radial direction upon further rotation of the cam 11 and to close the inlet into the coupling part 4 in a fluid-tight manner. The rotary valve or connector 5 can now be detached from the coupling piece 4 of the catheter 12, as shown in FIG. 8.

Figure 9:
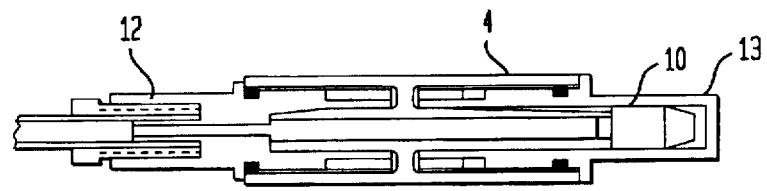

FIG. 9 shows the abdomen-side catheter section 12 being further secured by a protective cap 13 which is placed over the plug 10. Thus, the plug 10 cannot be unintentionally removed and is further secured in place.

Figure 10:
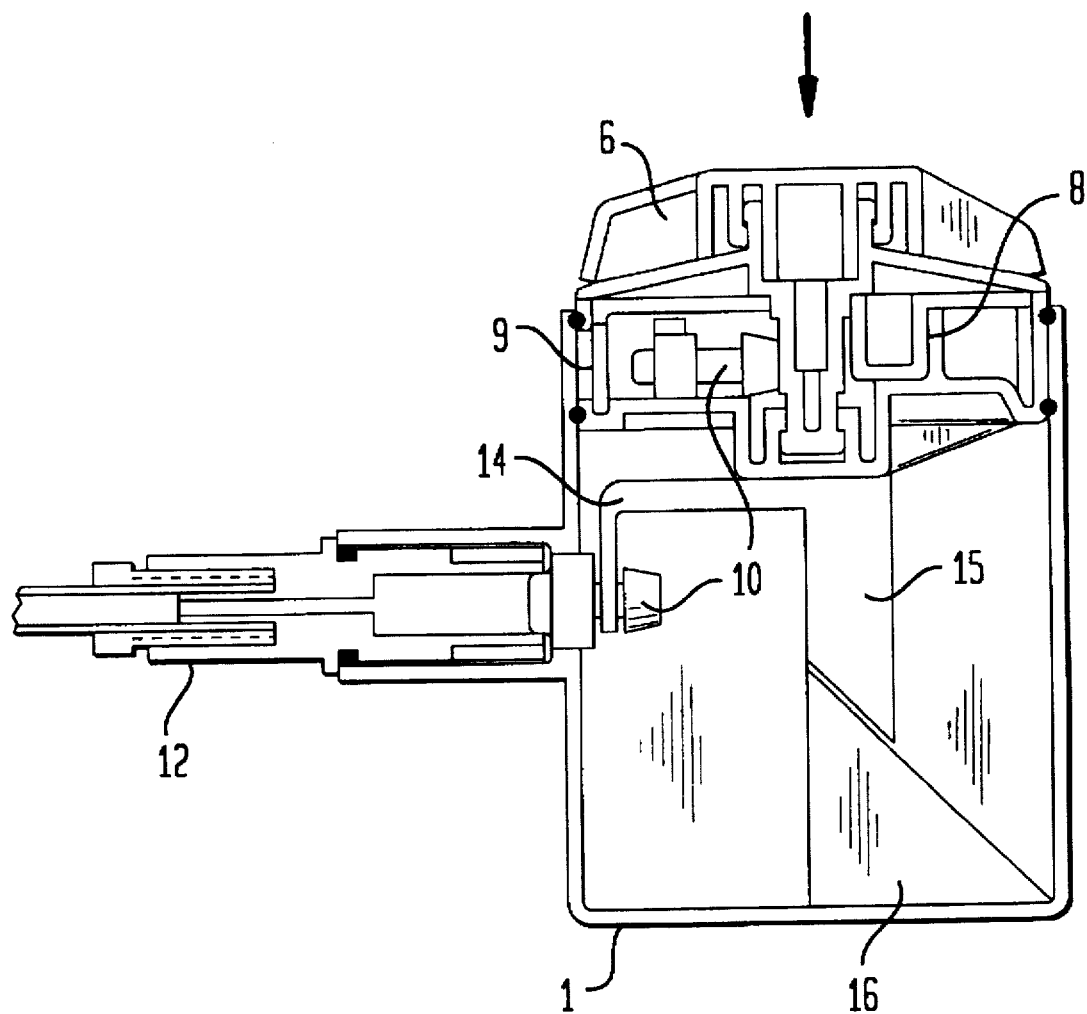
FIG. 10 is a vertical section of another embodiment of an apparatus for controlling a fluid flow in accordance with the present invention, illustrating in particular an extractor for removing a closure member from the peritoneal catheter.

Turning now to FIG. 10, there is shown a vertical section of another embodiment of an apparatus for controlling a fluid flow in accordance with the present invention, illustrating in particular an extractor 15 for removing the plug 10 from the peritoneal catheter 12. The extractor 15 is positioned underneath the rotatable assembly in direct contact therewith. At the end distant to the rotatable assembly, the extractor 15 is slanted to run upon a sloped surface of a support block 16. The extractor 15 is further formed with a cantilevered hook 14 which hooks behind the head of plug 10.

By applying a pressure on the grip portion in the direction indicated by the arrow, the extractor 15 slides downwards along the sloped surface 16 and is moved to the right to thereby extract the plug 10 from the coupling piece 4. As the rotary valve 5 is guided in the housing 1 for displacement in axial direction, continued application of pressure in direction of the arrow displaces the rotary valve 5 until being aligned with the fitting 3. Then the cycle as described above in connection with FIGS. 4 to 9 is repeated.

Figure 11:
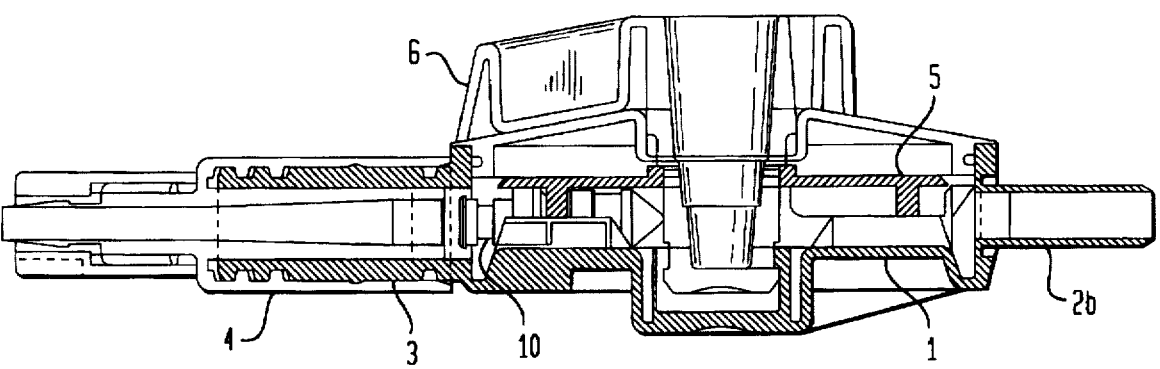
FIG. 11 is a sectional side view of still another embodiment of an apparatus for controlling a fluid flow in accordance with the present invention, with a fluid flow through each fitting being controlled by a separate closure member.
Figure 12:
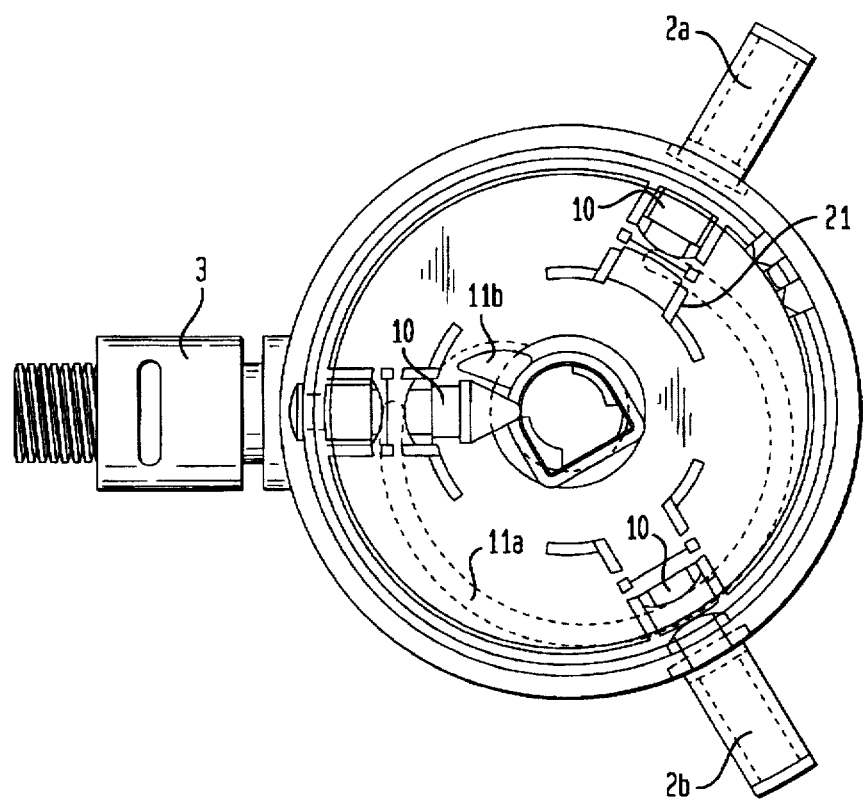
FIG. 12 is a sectional top view of the apparatus of FIG. 11.

FIGS. 11 and 12 show sectional side and top views of still another embodiment of an apparatus for controlling a fluid flow in accordance with the present invention, with each of the fittings 2a, 2b, 3 being closeable by a separate plug 10 which is displaceable in a radial direction. As the fluid flow through the fittings 2a, 2b, 3 is controlled by the plugs 10, the use of a separate blocking element 7 is eliminated. The displacement of the plugs 10 in radial direction is effected by securing the plugs 10 on a cam-like arcuated track 11a which is part of the rotatable assembly 5. Suitably, the plugs 10 are formed with grooves which engage the track 11a. In addition, the rotatable assembly 5 is connected to a wedge-shaped displacement member 11b which cooperates with the complementary end face of the plugs 10.

Thus, by turning the grip portion 6, the track 11a is advanced so that the plugs 10 in their cages 21 are displaced radially to open and close the fittings 2a, 2b, 3 in a same sequence as described previously with regard to FIGS. 3 to 9. The displacement is further supported by the displacement member 11b to effect a fluid-tight sealing of the fitting 3 as the end of the bag change. As the plugs 10 are moved radially in and out of the fittings 2a, 2b, 3, a separate extractor is not required.

While the invention has been illustrated and described as embodied in an apparatus for controlling a fluid flow, it is not intended to be limited to the details shown since various modification and structural changes may be made without departing in any way from the spirit of the present invention.

What is claimed as new and desired to be protected by Letters Patents is set forth in the appended claims:

1. Apparatus for controlling a fluid flow; comprising:
  a housing having at least three fittings for connection of three tubular elements;
  valve means rotatably secured in the housing and indexable in various predetermined positions for selectively establishing a fluid communication between the fittings, said valve means including a rotatable grip outside of said housing and a blocking element inside of said housing and connected to the grip, said blocking element formed with lateral openings and a passageway for allowing a fluid flow between two of the three fittings at one time; and at least one closure member received in the housing and associated to one of the fittings, said closure member being acted upon by the valve means for linear displacement in a radial direction to open and close a passage through said one fitting.

2. The apparatus of claim 1 wherein the housing has a cylindrical shape, said valve means including a rotatable grip and a cylindrical blocking element connected to the grip and formed with lateral openings for allowing a fluid flow between the fittings upon selectively indexing the blocking element in a predetermined position.

3. The apparatus of claim 1, and further comprising a second closure member moveable in radial direction by the valve means for opening and closing a passage through the other one of the fittings.

4. The apparatus of claim 2 wherein the blocking element and the closure member control a flow rate of fluid through the passage.

5. The apparatus of claim 1 wherein the valve means includes a cam for converting a rotation of the blocking element in a displacement of the closure member in radial direction.

6. The apparatus of claim 5 wherein the closure member is in connected in form-fitting manner with the cam.

7. The apparatus of claim 1 wherein the valve means includes an extractor for removing the closure member from the one fitting.

8. The apparatus of claim 7 wherein the extractor is formed by a track connected to the valve means, said plug being secured on the track so as to move in radial direction upon rotation of the valve means.

9. The apparatus of claim 1, and further comprising a protective cap for placement over the closure member.

10. The apparatus of claim 1, for use in peritoneal dialysis, with the a coupling element having one end secured to one fitting and another end secured to a peritoneal catheter, and further comprising locking means for preventing a detachment of the housing from the coupling piece and for preventing a detachment of the coupling piece from the peritoneal catheter.

11. The apparatus of claim 1 wherein the valve means is locked after one revolution.

12. The apparatus of claim 1 wherein the valve means is rotatable in only one direction of rotation, and further comprising monitoring means for surveying each sequence of rotation in optical and/or tactile manner.

13. A method of using an apparatus as connector for peritoneal dialysis, said apparatus comprising a housing having a first fitting for securement of a tube, a second fitting for seucrement of a second tube, and a third fitting for detachable securement of a coupling piece of a peritoneal catheter, valve means rotatably secured in the housing and indexable in various predetermined positions for selectively establishing a fluid communication between the fittings, said valve means including a rotatable grip outside of said housing and a blocking element inside of said housing and connected to the grip, said blocking element formed with lateral openings and a passageway for allowing a fluid flow between two of the three fittings at one time, and at least one closure member received in the housing and associated to one of the fittings, with the closure member being acted upon by the valve means for linear displacement in a radial direction to open and close a passage through the one fitting, said method comprising:

connecting a peritoneal catheter, a drain bag, and a source of irrigation fluid each to one of said three fittings;

dialyzing a patient by indexing the connector to permit flow from the source of irrigation fluid to the connector; and indexing the connector to permit flow from the catheter to the drain bag.

* * * * *